(12) United States Patent
Gillberg et al.

(10) Patent No.: US 9,586,052 B2
(45) Date of Patent: Mar. 7, 2017

(54) SYSTEMS AND METHODS FOR EVALUATING CARDIAC THERAPY

(71) Applicant: Medtronic, Inc., Minneapolis, MN (US)

(72) Inventors: Jeffrey Gillberg, Coon Rapids, MN (US); Subham Ghosh, Blaine, MN (US); Tarek Haddad, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/703,412

(22) Filed: May 4, 2015

(65) Prior Publication Data

US 2016/0045744 A1 Feb. 18, 2016

Related U.S. Application Data

(60) Provisional application No. 62/037,704, filed on Aug. 15, 2014.

(51) Int. Cl.
| | |
|---|---|
| *A61B 5/00* | (2006.01) |
| *A61N 1/372* | (2006.01) |
| *A61B 5/0408* | (2006.01) |
| *A61B 5/0452* | (2006.01) |
| *A61N 1/368* | (2006.01) |
| *A61N 1/365* | (2006.01) |

(52) U.S. Cl.
CPC ........ *A61N 1/37247* (2013.01); *A61B 5/0452* (2013.01); *A61B 5/04085* (2013.01); *A61N 1/3684* (2013.01); *A61B 5/4836* (2013.01); *A61N 1/3682* (2013.01); *A61N 1/3686* (2013.01); *A61N 1/36514* (2013.01)

(58) Field of Classification Search
CPC ............ A61N 1/37241; A61N 1/37247; A61N 1/3684; A61N 1/368; A61B 5/0452; A61B 5/04085; A61B 5/72; A61B 5/7253; A61B 5/7282
See application file for complete search history.

(56) References Cited

U.S. PATENT DOCUMENTS

| | | | |
|---|---|---|---|
| 4,233,987 | A | 11/1980 | Feingold |
| 4,402,323 | A | 9/1983 | White |
| 4,428,378 | A | 1/1984 | Anderson et al. |
| 4,497,326 | A | 2/1985 | Curry |
| 4,566,456 | A | 1/1986 | Koning et al. |

(Continued)

FOREIGN PATENT DOCUMENTS

| | | |
|---|---|---|
| CN | 1043621 A | 7/1990 |
| CN | 1253761 A | 5/2000 |

(Continued)

OTHER PUBLICATIONS

U.S. Appl. No. 14/173,288, filed Feb. 5, 2014, Sambelashvili.

(Continued)

*Primary Examiner* — Scott Getzow
(74) *Attorney, Agent, or Firm* — Carol F. Barry

(57) ABSTRACT

Systems and methods are described herein for assisting a user in evaluation of cardiac therapy. The systems and methods may monitor electrical activity of a patient using external electrode apparatus to provide baseline electrical heterogeneity information and therapy electrical heterogeneity information. The electrical heterogeneity information may be used to generate surrogate hemodynamic information.

26 Claims, 12 Drawing Sheets

(56) References Cited

U.S. PATENT DOCUMENTS

| | | |
|---|---|---|
| 4,593,702 A | 6/1986 | Kepski |
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,331,960 A | 7/1994 | Krenzke |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,810,740 A | 9/1998 | Paisner |
| 5,876,336 A | 3/1999 | Swanson et al. |
| 5,891,045 A | 4/1999 | Albrecht et al. |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb et al. |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |

(56) References Cited

U.S. PATENT DOCUMENTS

| | | |
|---|---|---|
| 9,320,446 B2 | 4/2016 | Gillberg et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Gosh et al. |
| 2012/0284003 A1 | 11/2012 | Gosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |

(56) References Cited

U.S. PATENT DOCUMENTS

| | | |
|---|---|---|
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0184590 A1 | 6/2016 | Gosh |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2016976 A1 | 1/2009 |
| EP | 2391270 A1 | 7/2011 |
| EP | 1 925 337 B1 | 3/2012 |
| EP | 2436309 A2 | 4/2012 |
| EP | 2 435 132 B1 | 8/2013 |
| WO | WO 98/26712 A1 | 6/1998 |
| WO | WO 99/06112 A1 | 2/1999 |
| WO | WO 00/45700 A1 | 8/2000 |
| WO | WO 01/67950 A1 | 9/2001 |
| WO | WO 03/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

U.S. Appl. No. 14/220,733, filed Mar. 20, 2014, Ghosh et al.
U.S. Appl. No. 14/227,719, filed Mar. 27, 2014, Gillberg et al.
U.S. Appl. No. 14/228,009, filed Mar. 27, 2014, Gillberg et al.
U.S. Appl. No. 14/228,024, filed Mar. 27, 2014, Ghosh et al.
U.S. Appl. No. 14/228,038, filed Mar. 27, 2014, Ghosh et al.
International Search Report and Written Opinion issued May 3, 2012 for International Application No. PCT/US2014/036262; 9 pages.
International Search Report and Written Opinion issued May 3, 2012 for International Application No. PCT/US2014/036302; 9 pages.
International Search Report and Written Opinion issued Aug. 6, 2014 for International Application No. PCT/US2014/036153; 14 pages.
International Search Report and Written Opinion issued Nov. 7, 2014 for International Application No. PCT/US2014/036163; 12 pages.
International Search Report and Written Opinion issued Oct. 28, 2014 for International Application No. PCT/US2014/041928; 15 pages.
International Search Report and Written Opinion issued Oct. 24, 2014 for International Application No. PCT/US2014/041929; 14 pages.
International Search Report and Written Opinion issued on Mar. 9, 2015 for International Application No. PCT/US2014/069214; 11 pages.
International Search Report and Written Opinion issued on Mar. 17, 2015, for International Application No. PCT/US2014/069192; 11 pages.
International Search Report and Written Opinion issued on Mar. 16, 2015 for International Application No. PCT/US2014/069182; 11 pages.
International Search Report and Written Opinion issued on Apr. 8, 2015 for International Application No. PCT/US2014/069070; 11 pages.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
"CardioGuide System Enables Real-Time Navigation of Left Ventricular Leads During Medtronic CRT Implants," Press Release, Apr. 9, 2013, Medtronic, Inc., 2 pgs.
Czerwinska et al., "Method of Segmentation of Thorax Organs Images Applied to Modeling the Cardiac Electrical Field," *Engineering in Medicine and Biology Society*, Proceedings of the $22^{nd}$ Annual International Conference of the IEEE, vol. 1, 23, Jul. 23, 2000.; pp. 402-405.
Freund et al., "A Decision-Theoretic Generalization of Online Learning and an Application to Boosting," *Journal of Computer and System Sciences*, 1997; 55(1):119-139.
Friedman, "Greedy Function Approximation: A Gradient Boosting Machine," *Annals of Statistics*, 2001; 29(5):1189-1232.
Friedman, "Stochastic Gradient Boosting," *Computational Statistics and Data Analysis*, 2002; 38(4):367-378.
Friedman et al., "Additive Logistic Regression: a Statistical View of Boosting," *Annals of Statistics*, 2000; 28(2):337-374.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.

(56) References Cited

OTHER PUBLICATIONS

Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
Hayes et al., "Cardiac Resynchronization Therapy and the Relationship of Percent Biventricular Pacing to Symptoms and Survival," *Heart Rhythm*, 2011, Sep.; 8(9):1469-1475.
"Heart Failure Management" datasheet [online]. Medtronic, Minneapolis, Minnesota, [Last updated on Jun. 3, 2013].Retrieved from the Internet: www.medtronic.com; 9 pages.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Ridgeway, "The State of Boosting," *Computing Science and Statistics*, 1999; 31:172-181.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-222.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Sperzel et al., "Intraoperative Characterization of Interventricular Mechanical Dyssynchrony Using Electroanatomic Mapping System—A feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms : a simulation study," Circulation Research, 1989, 64:449-462.
Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010; 121(5):626-634.
Turner et al, "Electrical and Mechanical Components of Dyssynchrony in Heart Failure Patients with Normal QRS Duration and Left Bundle-Branch Block," *Circulation* 2004; 109: 2544-2549.
Van Deursen et al., "Vectorcardiography as a Tool for Easy Optimization of Cardiac Resynchronization Therapy in Canine Left Bundle Branch Block Hearts," *Circulation Arrhythmia and Electrophysiology*, Jun. 1, 2012; 5(3):544-552.
Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.
Varma et al., "Placebo CRT," *Journal of Cardiovascular Electrophysiology*, vol. 19, Aug. 2008; p. 878.
Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.
Botker MD, PhD., et al., "Electromechanical Mapping for Detection of Myocardial Viability in Patients with ischemia Cardiomyopathy," Circulation, Mar. 2001; vol. 103, No. 12, pp. 1631-1637.
Cuculich, P.S., et al., "The Electrophysiological Cardiac Ventricular Substrate in Patients After Myocardial Infection" *J. Am. Coll. Cardiol.* 2011; 58:1893-1902.
Dawoud, F. et al., "Inverse Electrocardiographic Imaging to Assess Electrical Dyssynchrony in Cardiac Resynchronization Therapy Patients," *Computing in Cardiology*, 2012; 39:993-996.
Fung et al., Chapter 20, Optimization of Cardiac Resynchronization Therapy, Cardiac Resynchronization Therapy, Second Edition, Copyright 2008, Blackwell Publishing Ltd., pp. 356-373.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Hopenfeld et al., "The Effect of Conductivity on ST—Segment Epicardial Potentials Arising from Subendocardial Ischemia," Annals of Biomedical Eng., Jun. 2005; vol. 33, No. 6, pp. 751-763.
Medtronic Vitatron Carelink Encore® Programmer Model 29901 Reference Manual, 2013, Medtronic, Inc., Minneapolis, MN.
Miri et al., "Applicability of body surface potential map in computerized optimization of biventricular pacing," *Annals of Biomedical Engineering*, vol. 38, No. 3, Mar. 2010, pp. 865-875.
Miri et al., "Comparison of the electrophysiologically based optimization methods with different pacing parameters in patient undergoing resynchronization treatment," *30th Annual International IEEE EMBS Conference*, Aug. 2008, pp. 1741-1744.
Miri et al., "Computerized Optimization of Biventricular Pacing Using Body Surface Potential Map," *31st Annual International Conference of the IEEE EMBS*, Sep. 2009, pp. 2815-2818.
Miri et al., "Efficiency of Timing Delays and Electrode Positions in Optimization of Biventricular Pacing: A Simulation Study," *IEEE Transactions on Biomedical Engineering*, Nov. 2009, pp. 2573-2582.
Nash et al., "An Experimental-Computational Framework for Validating in-vivo ECG Inverse Algorithms," International Journal of Bioelectromagnetism, vol. 2, No. 2, Dec. 31, 2000, 9 pp.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" Circulation, 2013; 128: 2407-2418.
Strik et al., "Electrical and Mechanical Ventricular Activation During Left Bundle Branch Block and Resynchronization," *J. of Cardiovasc. Trans. Res.*, 2012; 5:117-126.
Svendsen et al., "Computational Models of Cardiac Electrical Activation," Chapter 5, Computational Nov. 2010, pp. 73-88.
Sweeney et al., QRS Fusion Complex Analysis Using Wave Interference to Predict Reverse Remodeling During Cardiac Resynchronization Therapy, heart Rhythm, 2014, 11:806-813.
Wang et al., "Application of the Method of Fundamental Solutions to Potential-based Inverse Electrocardiography," *Annals of Biomedical Engineering*, Aug. 2006, pp. 1272-1288.
Wellens, MD et al., "The Electrocardiogram 102 Years After Einthoven," Circulation, Feb. 2004; vol. 109, No. 5, pp. 562-564.

SYSTEMS AND METHODS FOR EVALUATING CARDIAC THERAPY

This application claims the benefit of U.S. Provisional Patent Application 62/037,704 entitled "Systems and Methods for Evaluating Cardiac Therapy" and filed on Aug. 15, 2014, which is incorporated herein by reference in its entirety.

The disclosure herein relates to systems and methods for use in the evaluation of cardiac therapy to be performed or being performed on a patient.

Cardiac therapy, such as cardiac resynchronization therapy (CRT), may correct symptoms of electrical dyssynchrony of a patient's heart by providing pacing therapy to one or both ventricles or atria, e.g., by providing pacing to encourage earlier activation of the left or right ventricles. By pacing the ventricles, the ventricles may be controlled such that they contract in synchrony.

Providing cardiac therapy to a patient may involve determining effective and/or optimal pacing locations (e.g., locations for delivering pacing therapy) and determining effective programming of device parameters. During implantation, the location of one or more electrodes may be adjusted to be positioned in an effective and/or optimal location to deliver pacing therapy to the patient (e.g., for CRT). Further, during or after implantation, one or more different pacing vectors may be selected to deliver effective and/or optimal pacing therapy to the patient (e.g., for CRT). Additionally, the selection of the timing of the pacing pulses delivered to the electrodes, such as atrioventricular (AV) and interventricular (VV) delays, may also be adjusted to deliver effective and/or optimal pacing therapy.

SUMMARY

The exemplary systems, methods, and interfaces described herein may be configured to assist a user (e.g., a physician) in evaluating cardiac therapy (e.g., cardiac therapy being performed on a patient during and/or after implantation of cardiac therapy apparatus). The systems, methods, and interfaces may be described as being noninvasive. For example, the systems, methods, and interfaces may not need, or include, implantable devices such as leads, probes, sensors, catheters, etc. to evaluate cardiac therapy. Instead, the systems, methods, and interfaces may use electrical measurements taken noninvasively using, e.g., a plurality of external electrodes attached to the skin of a patient about the patient's torso.

The exemplary systems and methods may monitor baseline electrical activity (e.g., no cardiac therapy is delivered during baseline monitoring) and therapy electrical activity using a plurality of external electrodes during the delivery of cardiac therapy from the patient. Electrical heterogeneity information (e.g., data) may be generated for each of the baseline electrical activity and the therapy electrical activity. The electrical heterogeneity information (e.g., data) may include a global metric generated from electrical activity monitored by all of the electrodes and at least one local, or regional, metric generated from electrical activity monitored by a portion, or set, of the electrodes. The electrical heterogeneity information (e.g., data) may be input into a transfer function that generates surrogate electrical hemodynamic response information representative of the hemodynamic response to the pacing therapy delivered. In at least one embodiment, the surrogate electrical hemodynamic response information may include a single value indicative of the hemodynamic response, or effectiveness, of the pacing therapy.

A user may use the surrogate electrical hemodynamic response information to determine whether the pacing therapy should be further configured, or re-configured. For example, a user may move one or more pacing electrodes or change one or more pacing vectors to use one or more different pacing electrodes. Further, for example, the user may change one or more pacing settings such as, e.g., A-V intervals, V-V intervals, pacing output power, etc.

The exemplary systems and methods may be used prior to implantation of cardiac therapy apparatus, during implantation of cardiac therapy apparatus, and/or after implantation of cardiac therapy apparatus. More specifically, the exemplary systems and methods may be used to evaluate the cardiac health of a patient prior to cardiac therapy, during the initial configuration of cardiac therapy, and after initial configuration of cardiac therapy in a follow-up appointment.

One exemplary system for use in evaluation of cardiac therapy may include electrode apparatus and computing apparatus coupled to the electrode apparatus. The electrode apparatus may include a plurality of external electrodes configured to be located proximate tissue of a patient (e.g., plurality of external electrodes comprises surface electrodes positioned in an array configured to be located proximate the skin of the torso of the patient). The plurality of electrodes may include two or more left external electrodes configured to be located proximate the left side of the patient. The computing apparatus may be configured to monitor baseline electrical activity using the plurality of external electrodes, monitor therapy electrical activity using the plurality of external electrodes during delivery of pacing therapy (e.g., pacing therapy is delivered by at least one implantable electrode coupled to at least one lead) using a selected pacing configuration (e.g., one or more pacing settings such as one or more of A-V intervals, V-V intervals, pacing vectors (e.g., multipoint pacing vectors), pacing energy outputs, pacing locations, multipoint pacing timing, cathode location, etc.), and generate electrical heterogeneity information representative of at least one of mechanical cardiac functionality and electrical cardiac functionality for each of the baseline electrical activity and the therapy electrical activity. The electrical heterogeneity information may include a global metric based on the electrical activity monitored by the plurality of external electrodes (e.g., a global standard deviation of surrogate electrical activation times monitored by the plurality of external electrodes) and at least one local metric based on the electrical activity monitored by the two or more left external electrodes (e.g., a left standard deviation of surrogate electrical activation times monitored by the two or more left external electrodes, a left average of surrogate electrical activation times monitored by the two or more left external electrodes, etc.). The computing apparatus may be further configured to generate surrogate hemodynamic response information representative of the hemodynamic response to the pacing therapy delivered using the selected pacing configuration based on the electrical heterogeneity information for each of the baseline electrical activity and the therapy electrical activity (e.g., a hemodynamic response value representative of the hemodynamic improvement due to the pacing therapy delivered using the selected pacing configuration).

One exemplary method for use in evaluation of cardiac therapy may include monitoring baseline electrical activity using a plurality of external electrodes (e.g., plurality of external electrodes comprises surface electrodes positioned in an array configured to be located proximate the skin of the torso of the patient), monitoring therapy electrical activity using the plurality of external electrodes during delivery of pacing therapy (e.g., pacing therapy is delivered by at least one implantable electrode coupled to at least one lead) using a selected pacing configuration (e.g., one or more pacing settings such as one or more of A-V intervals, V-V intervals, pacing vectors (e.g., multipoint pacing vectors), pacing energy outputs, pacing locations, multipoint pacing timing, cathode location, etc.), generating electrical heterogeneity information representative of at least one of mechanical cardiac functionality and electrical cardiac functionality for each of the baseline electrical activity and the therapy electrical activity. The electrical heterogeneity information may include a global metric based on the electrical activity monitored by the plurality of external electrodes (e.g., a global standard deviation of surrogate electrical activation times monitored by the plurality of external electrodes) and at least one local metric based on the electrical activity monitored by the two or more left external electrodes (e.g., a left standard deviation of surrogate electrical activation times monitored by the two or more left external electrodes, a left average of surrogate electrical activation times monitored by the two or more left external electrodes, etc.). The exemplary method may further include generating surrogate hemodynamic response information representative of the hemodynamic response to the pacing therapy delivered using the selected pacing configuration based on the electrical heterogeneity information for each of the baseline electrical activity and the therapy electrical activity (e.g., a hemodynamic response value representative of the hemodynamic improvement due to the pacing therapy delivered using the selected pacing configuration).

One exemplary system for use in evaluation of cardiac therapy may include electrode means and computing means. The electrode means may include a plurality of external electrodes configured to be located proximate tissue of a patient (e.g., plurality of external electrodes comprises surface electrodes positioned in an array configured to be located proximate the skin of the torso of the patient). The computing means may be for monitoring baseline electrical activity using the electrodes means, monitoring therapy electrical activity using the electrodes means during delivery of pacing therapy (e.g., pacing therapy is delivered by at least one implantable electrode coupled to at least one lead) using a selected pacing configuration (e.g., one or more pacing settings such as one or more of A-V intervals, V-V intervals, pacing vectors (e.g., multipoint pacing vectors), pacing energy outputs, pacing locations, multipoint pacing timing, cathode location, etc.), and generating electrical heterogeneity information representative of at least one of mechanical cardiac functionality and electrical cardiac functionality for each of the baseline electrical activity and the therapy electrical activity. The electrical heterogeneity information may include a global metric based on the electrical activity monitored by the plurality of external electrodes (e.g., a global standard deviation of surrogate electrical activation times monitored by the plurality of external electrodes) and at least one local metric based on the electrical activity monitored by the two or more left external electrodes (e.g., a left standard deviation of surrogate electrical activation times monitored by the two or more left external electrodes, a left average of surrogate electrical activation times monitored by the two or more left external electrodes, etc.). The computing means may be further for generating surrogate hemodynamic response information representative of the hemodynamic response to the pacing therapy delivered using the selected pacing configuration based on the electrical heterogeneity information for each of the baseline electrical activity and the therapy electrical activity (e.g., a hemodynamic response value representative of the hemodynamic improvement due to the pacing therapy delivered using the selected pacing configuration).

In one or more embodiments generating hemodynamic response information representative of the hemodynamic response to the pacing therapy delivered using the selected pacing configuration based on the electrical heterogeneity information for each of the baseline electrical activity and the therapy electrical activity may include providing a transfer function configured to receive the global metric and the at least one local metric to generate surrogate hemodynamic response information correlating to left ventricular contractility, wherein the transfer function provides a coefficient of determination ($R^2$) between the surrogate hemodynamic response information and the left ventricular contractility that is greater than or equal to 60%, inputting the global metric and the at least one local metric into the transfer function, and generating the hemodynamic response information correlating to left ventricular contractility using the transfer function based on the global metric and the at least one local metric.

In one or more embodiments, the hemodynamic response information may be configured to assist a user in noninvasively selecting an implant location for the at least one implantable electrode coupled to the at least one lead.

In one or more embodiments, it may be determined whether the pacing therapy using the pacing configuration is acceptable if the hemodynamic response value is greater than or equal to a threshold value.

In one or more embodiments, display apparatus may include a graphical user interface configured to present information for use in assisting a user in evaluating cardiac pacing location, and the hemodynamic response information (e.g., one or more values, graphical representations, etc.) may be displayed on the graphical user interface.

The exemplary systems and methods may use an electrocardiogram (ECG) belt that may involve at least one row of electrodes on each of anterior and posterior surfaces of the torso, approximately encircling the heart. Each electrode on the belt may record a unipolar ECG from which an activation time can be obtained. Three metrics of electrical heterogeneity may be derived, or generated from the unipolar ECG recordings: a standard deviation of activation times from all electrodes on the belt (SDAT), a left ventricular electrical dyssynchrony computed as standard deviation of activation times from electrodes on the left-side (LVED), and an average left ventricular activation time computed as the mean electrical activation time of the left sided electrodes (LVAT).

Of particular interest may be the changes in three electrical heterogeneity metrics from the ECG belt from baseline (underlying) rhythm to CRT pacing. For example, the criteria of electrical resynchronization, or response, from ECG belt may include a reduction in two or more metrics by more than 10% without the global metric (SDAT) increasing by more than 10% from baseline to cardiac pacing. One or more embodiments may use a transfer function model that generates a single variable reflective of hemodynamic response to pacing based on relative changes in the three heterogeneity metrics from baseline to pacing. The output from this model can be used to determine an optimal pacing location or vector (from a multipolar lead system). Further, the model can be also used to visualize how response changes as a physician maps different areas of the left ventricle for finding the optimal site location.

The exemplary transfer function model may be described as a function that takes in changes in three electrical heterogeneity metrics from an ECG belt from baseline to CRT pacing and outputs a single variable that is a surrogate of acute hemodynamic response. A physician can map multiple locations in the left heart by pacing acutely, and the exemplary transfer function model may generate a variable reflecting the acute hemodynamic response to pacing for each site. The physician can then proceed to select the side that gives the best hemodynamic response, or a site that gives a response above a certain threshold value (e.g., a 15% improvement in hemodynamics).

The exemplary transfer function may be described as a non-linear transfer function. In at least one embodiment, the transfer function may include a correlation greater than or equal to about 70% between the predicted data, or predicted hemodynamic response, and actual data, or actual hemodynamic response. For example, the transfer function may have a coefficient of determination ($R^2$) between surrogate hemodynamic response information and the left ventricular contractility (e.g., maximum left ventricular pressure rate) that is greater than or equal to 60%.

For a lead with multiple LV electrodes and pacing vectors, the transfer function model can be used to rank order vectors and settings in terms of acute hemodynamic response. The settings could involve different AV or VV delays and/or different pacing vectoring of a combination of LV pacing vectors (multipoint LV pacing). Acute hemodynamic response may be an effective strategy for selecting LV pacing sites, pacing vectors, and/or other settings for resynchronization therapy. Acute hemodynamic response, however, requires an invasive pressure sensor in the left heart cavity. The exemplary systems and methods described herein may use a transfer function model that takes metrics of electrical heterogeneity from an ECG belt and transforms the metrics into a surrogate of hemodynamic response. The transfer function model has a high correlation with invasively recorded hemodynamics from a left heart pressure catheter. As such, the exemplary systems and methods may be useful in comparing hemodynamic efficacy of different LV pacing sites and/or vectors without having to put in a left heart pressure catheter in the patient's left heart cavity.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
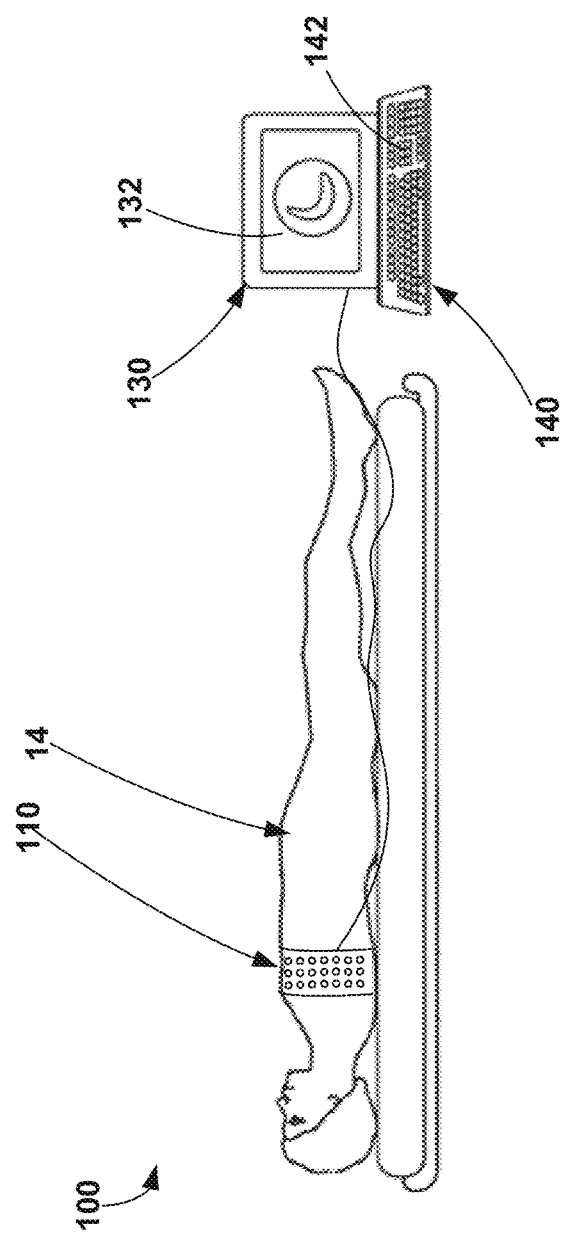
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods shall be described with reference to FIGS. 1-10. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Cardiac electrical activation times can be detected or estimated in proximity of a reference location (e.g., which can be a chosen location for the left ventricle lead during implant) using unipolar electrocardiogram (ECG) recordings. Such electrical activation times may be measured and displayed, or conveyed, to an implanter by a system which acquires the ECG signals and generates the metric of electrical activation times (e.g., depolarization) measured from various ECG locations. As described herein, at least in one or more embodiments, electrical activation times displayed on a graphical user interface may be used in noninvasive evaluation of cardiac therapy.

Various exemplary systems, methods, and interfaces may be configured to use electrode apparatus including external electrodes, display apparatus, and computing apparatus to noninvasively assist a user (e.g., a physician) in the evaluation of cardiac therapy. An exemplary system 100 including electrode apparatus 110, display apparatus 130, and computing apparatus 140 is depicted in FIG. 1.

The electrode apparatus 110 as shown includes a plurality of electrodes incorporated, or included, within a band wrapped around the chest, or torso, of a patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Exemplary electrode apparatus may be described in U.S. patent application Ser. No. 14/227,719 entitled "Bioelectric Sensor Device and Methods" and filed Mar. 27, 2014, which is incorporated herein by reference in its entirety. Further, exemplary electrode apparatus 110 will be described in more detail in reference to FIGS. 2-3.

Although not described herein, the exemplary system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the exemplary systems, methods, and interfaces described herein may further use imaging apparatus to provide noninvasive assistance to a user (e.g., a physician) to locate or select a pacing electrode or pacing vector proximate the patient's heart in conjunction with the evaluation of cardiac therapy.

For example, the exemplary systems, methods, and interfaces may provide image guided navigation that may be used to navigate leads including electrodes, leadless electrodes, wireless electrodes, catheters, etc., within the patient's body while also providing noninvasive cardiac therapy evaluation including determining location information (e.g., location information for the electrodes). Exemplary systems and methods that use imaging apparatus and/or electrode apparatus may be described in U.S. patent application Ser. No. 13/916,353 filed on Jun. 12, 2013 and entitled "Implantable Electrode Location Selection," U.S. patent application Ser. No. 13/916,377 filed on Jun. 12, 2013 and entitled "Implantable Electrode Location Selection," U.S. patent application Ser. No. 14/227,955 filed on Mar. 27, 2014 and entitled "Systems, Methods, and Interfaces for Identifying Effective Electrodes," U.S. patent application Ser. No. 14/227,919 filed on Mar. 27, 2014 and entitled "Systems, Methods, and Interfaces for Identifying Optimal Electrical Vectors," each of which is incorporated herein by reference in its entirety.

Exemplary imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate treatment apparatus proximate target locations within the heart or other areas of interest.

Systems and/or imaging apparatus that may be used in conjunction with the exemplary systems and methods described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 130 and the computing apparatus 140 may be configured to display and analyze data such as, e.g., electrical signals (e.g., electrocardiogram data), electrical heterogeneity information (e.g., data) representative of at least one of mechanical cardiac functionality and electrical cardiac functionality, etc. Electrical heterogeneity information (e.g., data) may include, e.g., electrical dyssynchrony information, surrogate electrical activation information or data, etc. that is generated using electrical signals gathered, monitored, or collected, using the electrode apparatus 110. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in evaluating a pacing configuration (e.g., the location of an implantable electrode used for pacing, the location of pacing therapy delivered by a particular pacing vector, one or more parameters of the pacing, etc.).

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 and to view and/or select one or more pieces of information related to the cardiac therapy.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including cardiac information, textual instructions, graphical depictions of electrical activation information, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, electrical signal/waveform data from the electrode apparatus 110, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high level procedural and/or object orientated programming language that is suitable for communicating with a computer system.

Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, mini computer, tablet computer, etc.). The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

Figure 2:
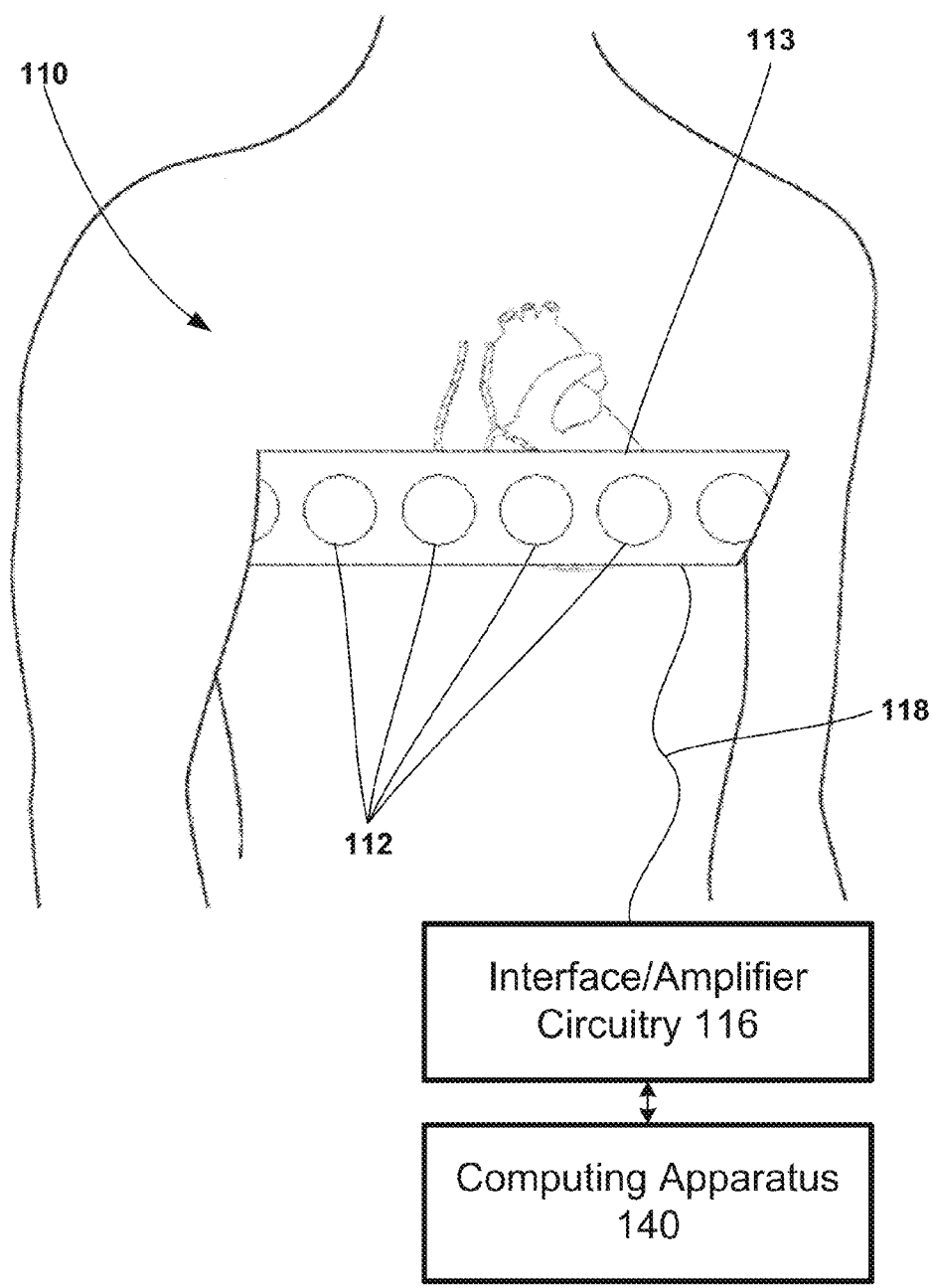
FIGS. 2-3 are diagrams of exemplary external electrode apparatus for measuring torso-surface potentials.

Electrical activation times of the patient's heart may be useful to evaluate cardiac therapy being delivered to a patient. Surrogate electrical activation information or data of one or more regions of a patient's heart may be monitored, or determined, using electrode apparatus 110 as shown in FIG. 1 and in FIGS. 2-3. The exemplary electrode apparatus 110 may be configured to measure body-surface potentials of a patient 14 and, more particularly, torso-surface potentials of a patient 14. As shown in FIG. 2, the exemplary electrode apparatus 110 may include a set, or array, of electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, anterolateral, and anterior locations of the torso of a patient 14.

Further, the electrodes 112 may be electrically connected to interface/amplifier circuitry 116 via wired connection 118.

The interface/amplifier circuitry 116 may be configured to amplify the signals from the electrodes 112 and provide the signals to the computing apparatus 140. Other exemplary systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 14. Further, in other examples, electrodes 112 (e.g., arranged in an array) may be part of, or located within, patches, vests, and/or other manners of securing the electrodes 112 to the torso of the patient 14. Still further, in other examples, the electrodes 112 may be part of, or located within, two sections of material or two "patches." One of the two sections or patches may be located on the anterior side of the torso of the patient 14 (to, e.g., monitor electrical signals representative of the anterior side of the patient's heart, measure surrogate cardiac electrical activation times representative of the anterior side of the patient's heart) and the other section or patch may be located on the posterior side of the torso of the patient 14 (to, e.g., monitor electrical signals representative of the posterior side of the patient's heart, measure surrogate cardiac electrical activation times representative of the posterior side of the patient's heart).

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of patient. Other configurations may have more or fewer electrodes 112.

The computing apparatus 140 may record and analyze the torso-surface potential signals sensed by electrodes 112 and amplified/conditioned by the interface/amplifier circuitry 116. The computing apparatus 140 may be configured to analyze the signals from the electrodes 112 to provide surrogate electrical activation information or data such as surrogate cardiac electrical activation times, e.g., representative of actual, or local, electrical activation times of one or more regions of the patient's heart as will be further described herein. For example, electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the postero-lateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and the next onset of cardiac depolarization. In one or more embodiments, measurement of activation times can be performed by picking an appropriate fiducial point (e.g., peak values, minimum values, minimum slopes, maximum slopes, zero crossings, threshold crossings, etc. of a near or far-field EGM) and measuring time between fiducial points (e.g., within the electrical activity).

Additionally, the computing apparatus 140 may be configured to provide graphical user interfaces depicting the surrogate electrical activation times obtained using the electrode apparatus 110. Exemplary systems, methods, and/or interfaces may noninvasively use the electrical information collected using the electrode apparatus 110 to evaluate cardiac therapy being delivered to the patient.

Figure 3:
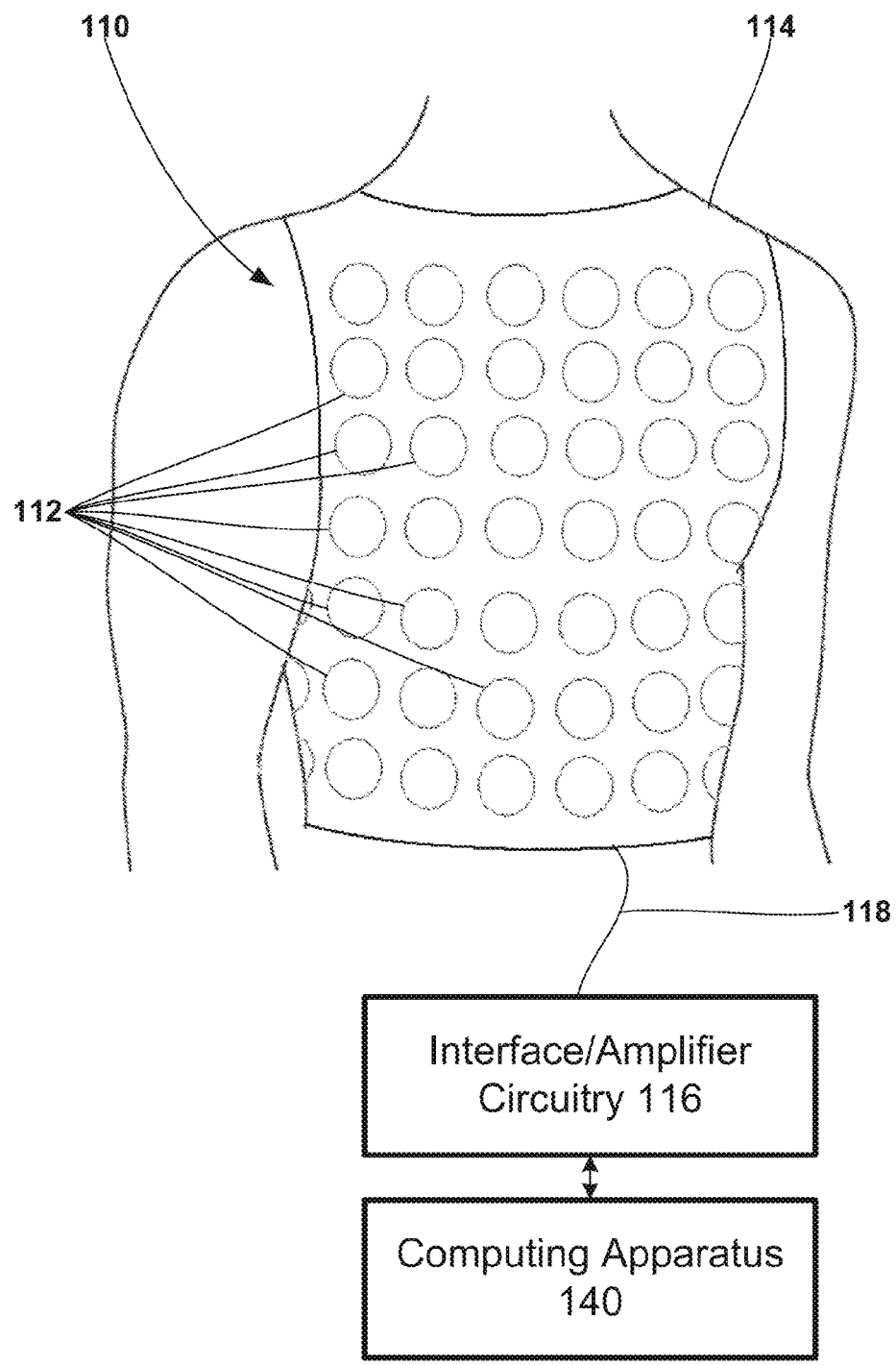

FIG. 3 illustrates another exemplary electrode apparatus 110 that includes a plurality of electrodes 112 configured to surround the heart of the patient 14 and record, or monitor, the electrical signals associated with the depolarization and repolarization of the heart after the signals have propagated through the torso of the patient 14. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 14, including, for example, the anterior, lateral, posterolateral, anterolateral, and posterior surfaces of the torso of the patient 14.

The vest 114 may be formed of fabric with the electrodes 112 attached to the fabric. The vest 114 may be configured to maintain the position and spacing of electrodes 112 on the torso of the patient 14. Further, the vest 114 may be marked to assist in determining the location of the electrodes 112 on the surface of the torso of the patient 14. In some examples, there may be about 25 to about 256 electrodes 112 distributed around the torso of the patient 14, though other configurations may have more or fewer electrodes 112.

As described herein, the electrode apparatus 110 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart.

The exemplary systems, methods, and interfaces may be used to provide noninvasive assistance to a user in the evaluation of cardiac health of a patient and/or cardiac therapy being delivered to the patient (e.g., cardiac therapy being presently-delivered to a patient during implantation or after implantation). Further, the exemplary systems, methods, and interfaces may be used to assist a user in the evaluation and configuration of the cardiac therapy being delivered to a patient (e.g., either during an initial configuration or one or more follow-up appointments).

Figure 4:
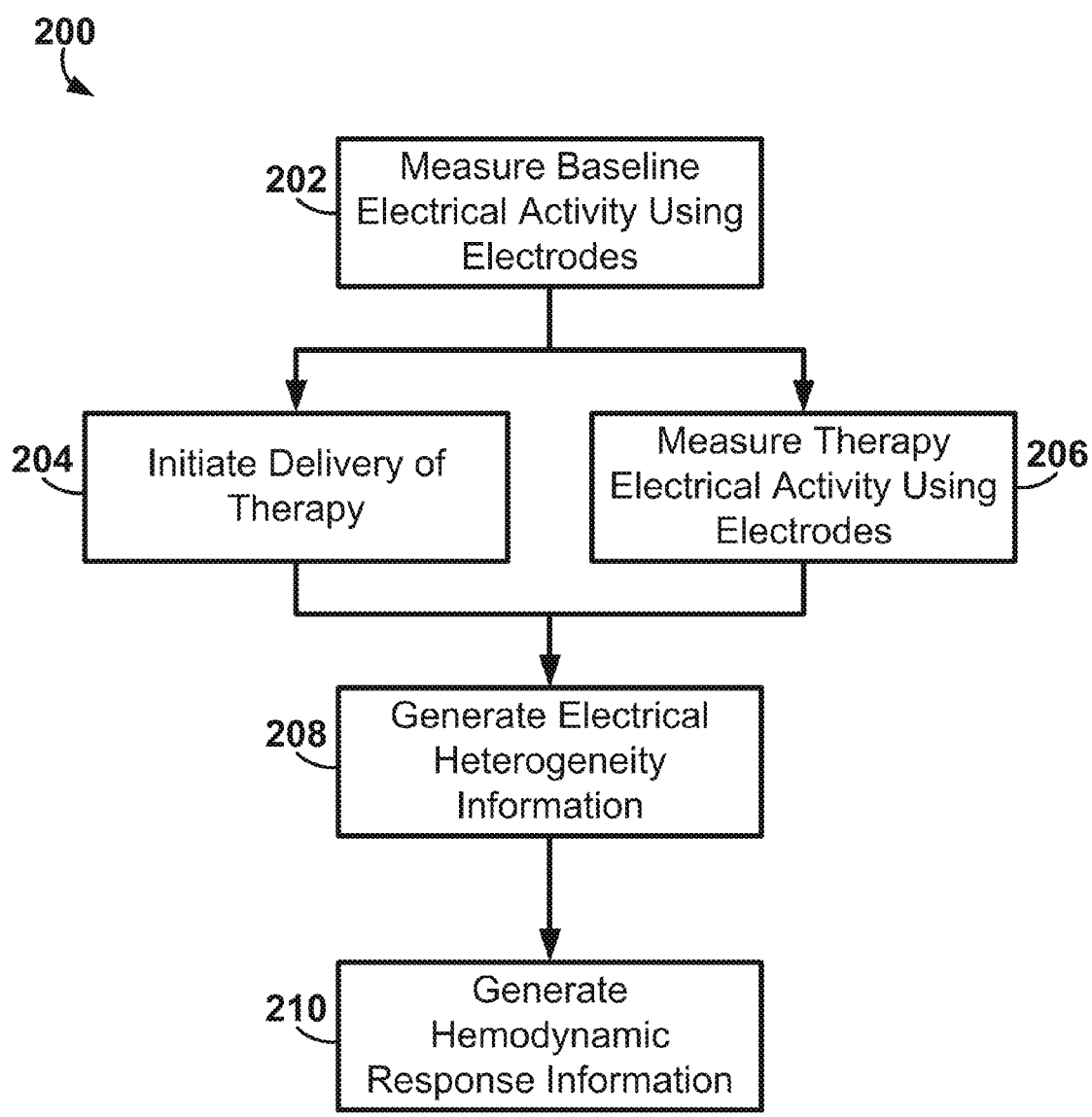
FIG. 4 is a block diagram of an exemplary method for cardiac therapy evaluation.

Exemplary method 200 depicted in FIG. 4 may be used to provide this functionality. The exemplary method 200 may be generally described to be used in the noninvasive evaluation of cardiac therapy. The exemplary method 200 may be described as being noninvasive because the method does not use invasive apparatus to perform the evaluation of the cardiac therapy. The cardiac therapy being delivered, however, may be described as being invasive such as when, e.g., one or more pacing electrodes are implanted proximate a patient's heart. The exemplary method 200 may be used to evaluate and/or configure such invasive cardiac therapy.

The exemplary method 200 may include monitoring, or measuring, electrical activity using a plurality of external electrodes 202. The electrical activity monitored during process 202 may be referred to as "baseline" electrical activity because no therapy is delivered to the patient such that the patient's heart is in its natural, or intrinsic, rhythm.

The plurality of external electrodes may be similar to the external electrodes provided by the electrode apparatus 110 as described herein with respect to FIGS. 1-3. For example, the plurality of external electrodes may be part, or incorporated into, a vest or band that is located about a patient's torso. More specifically, the plurality of electrodes may be described as being surface electrodes positioned in an array configured to be located proximate the skin of the torso of a patient.

Similar to process 202, the exemplary method 200 may include monitoring, or measuring, electrical activity using a plurality of external electrodes 206 during the delivery of the cardiac therapy 204. The electrical activity may be referred to as "therapy" electrical activity because cardiac therapy is being delivered to the patient while the electrical activity is being monitored. The plurality of external electrodes may be the same electrodes used to monitor baseline electrical activity 202 and may be located in the same location, or position, as the same electrodes used to monitor baseline electrical activity 202 (e.g., the electrodes may not have been moved, removed, or repositioned after monitoring baseline electrical activity 202). The electrodes may be similar to the external electrodes provided by the electrode apparatus 110 as described herein with respect to FIGS. 1-3.

The exemplary method 200 may initiate delivery of cardiac therapy 204 such as, e.g., cardiac pacing therapy. The cardiac therapy 204 may be delivered by at least one implantable electrode coupled to at least one lead. In at least one embodiment, the cardiac therapy 204 may be delivered by a lead-less electrode. Exemplary cardiac therapy may be further described herein with reference to FIGS. 8-10. As described herein, although the cardiac therapy delivery may be described as being invasive, the exemplary method 200 may be described as noninvasive because the exemplary method 200 may only initiate the delivery of the cardiac therapy and further uses electrical signals that are monitored, or taken, from the patient noninvasively.

The cardiac therapy may be delivered 204 at a selected pacing configuration. The pacing configuration may include one or more parameters related to the cardiac pacing that may be changed, or modified, by a user to, in effect, change the pacing therapy. The pacing configuration may be described as being a "selected" pacing configuration because a user (e.g., a physician) may select and configure pacing apparatus with the one or more parameters for the pacing configuration.

The pacing configuration may include a pacing location or pacing vector. The pacing location, or the location(s) at which the pacing is delivered, may be changed in multiple ways. For example, one or more electrodes used for pacing (cathodes or anodes) may be physically moved to change, or adjust, the pacing location. If the pacing electrodes are attached, or coupled, to a lead, the lead may be moved. Further, for example, a different set of electrodes may be used for pacing to change, or adjust, the pacing location. For instance, a lead may include multiple electrodes that may be enabled or disabled for use in a pacing vector, and different combinations of the multiple electrodes may be used in different pacing vectors. In this way, the pacing location may be changed without physically moving any pacing electrodes. Further, multipoint pacing vectors may be described as involving multiple left ventricular pacing sites and/or multiple right ventricular pacing sites.

The pacing configuration may further include a plurality of different pacing modes. For example, the pacing modes may include left univentricular pacing, biventricular pacing, tri-ventricular pacing, right ventricular synchronized only pacing, multi-site pacing, etc.

The pacing configuration may further include a plurality of different pacing settings. For example, the pacing settings may include one or more settings related to pacing time periods or timings, one or more settings related to pacing output power, etc. The settings related to pacing time periods may include AV interval (e.g., the time period between an atrial event and a ventricular pace), VV interval (e.g., the time period between a right ventricular pace and a left ventricular pace), LV-to-LV interval (e.g., time period between 2 left ventricular paces), LV pre-excitation value (e.g., left ventricular pacing relative to a right ventricular sense), etc. The settings related to pacing output power may include pulse width, pulse duration, number of pulses, pulse amplitude, pacing voltage, pulse waveshape, etc.

Figure 6:
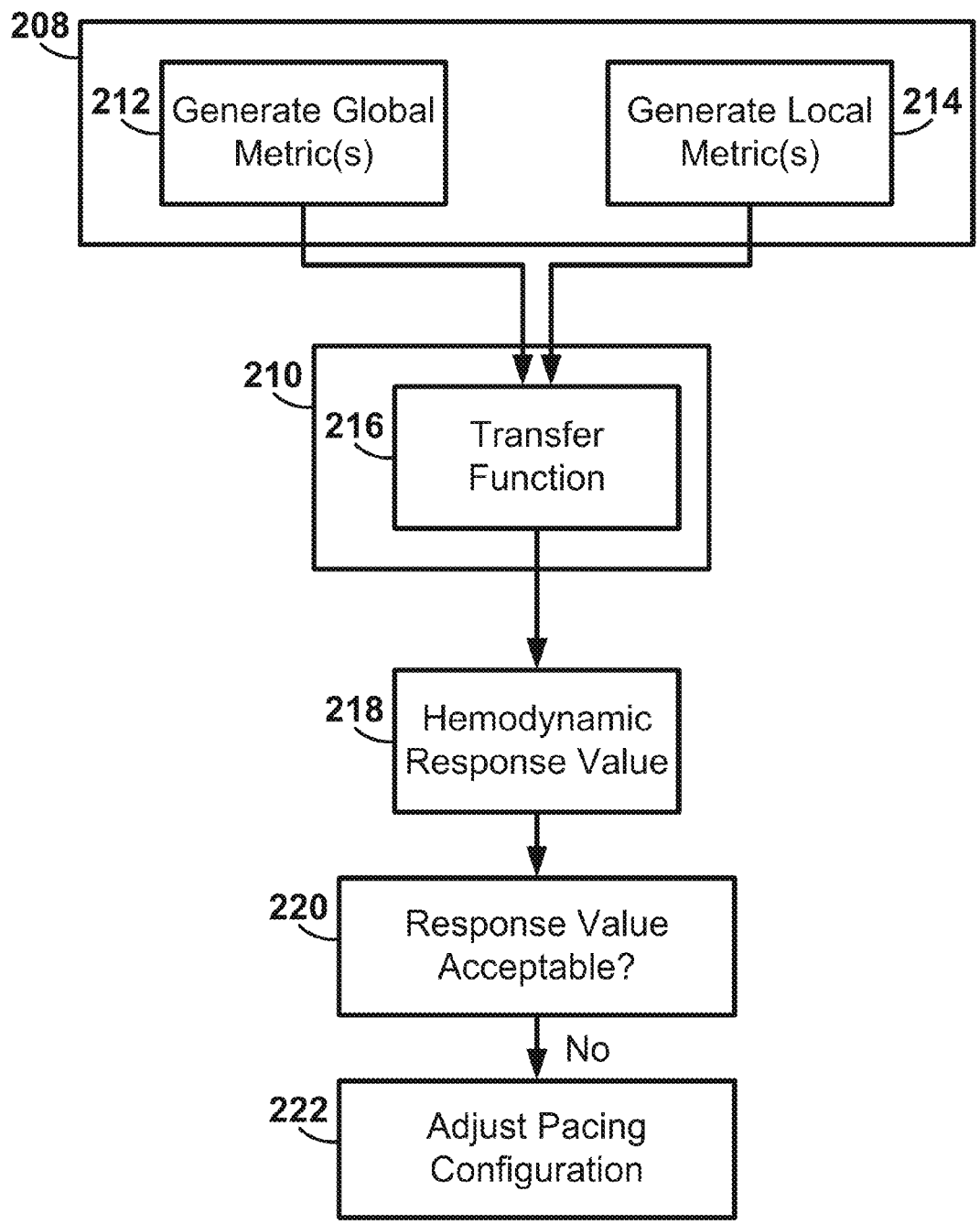
FIG. 6 is a more detailed block diagram of a portion of the exemplary method of FIG. 4 and additional processes for cardiac therapy evaluation.

A user may modify, or adjust, the pacing configuration by modifying, or adjusting, one or more of the parameters of the pacing configuration if, for example, the present pacing configuration is determined to be unacceptable as will be further described herein with respect to FIG. 6.

The monitored baseline electrical activity 202 and therapy electrical activity 206 may be used to generate electrical heterogeneity information (e.g., data). The electrical heterogeneity information may be described as information, or data, representative of at least one of mechanical cardiac functionality and electrical cardiac functionality. Electrical heterogeneity information and other cardiac therapy information may be described in U.S. Provisional Patent Application No. 61/834,133 entitled "METRICS OF ELECTRICAL DYSSYNCHRONY AND ELECTRICAL ACTIVATION PATTERNS FROM SURFACE ECG ELECTRODES" and filed on Jun. 12, 2013, which is hereby incorporated by reference it its entirety.

Electrical heterogeneity information may be further defined as information indicative of at least one of mechanical synchrony or dyssynchrony of the heart and/or electrical synchrony or dyssynchrony of the heart. In other words, electrical heterogeneity information may represent a surrogate of actual mechanical and/or electrical functionality.

In at least one embodiment, the electrical heterogeneity information may include a standard deviation of ventricular activation times corresponding to some or all of the external electrodes, e.g., of the electrode apparatus 110. Further, regional electrical heterogeneity information may be include standard deviations and/or averages of activation times corresponding to electrodes located in certain anatomic areas of the torso. The electrical heterogeneity information may be generated using one or more various systems and/or methods. Electrical heterogeneity information may be generated using an array, or a plurality, of surface electrodes and/or imaging systems as described in U.S. Pat. App. Pub. No. 2012/0283587 A1 published Nov. 8, 2012 and entitled "ASSESSING INRA-CARDIAC ACTIVATION PATTERNS AND ELECTRICAL DYSSYNCHRONY," U.S. Pat. App. Pub. No. 2012/0284003 A1 published Nov. 8, 2012 and entitled "ASSESSING INTRA-CARDIAC ACTIVATION PATTERNS", and U.S. Pat. No. 8,180,428 B2 issued May 15, 2012 and entitled "METHODS AND SYSTEMS FOR USE IN SELECTING CARDIAC PACING SITES," each of which is incorporated herein by reference in its entirety.

Electrical heterogeneity information (e.g., data) may include one or more global and/or local metrics or indices. For example, one of the global metrics, or indices, of electrical heterogeneity may be a standard deviation of activation-times (SDAT) measured by some or all of the electrodes on the surface of the torso of patient. In some examples, the SDAT may be calculated using the estimated cardiac activation times over the surface of a model heart.

Figure 5:
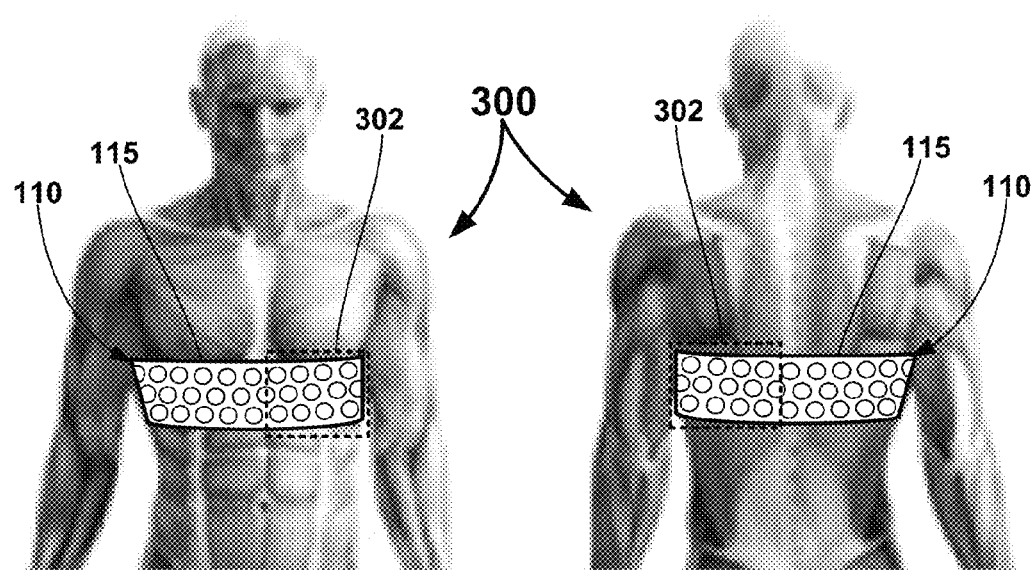
FIG. 5 is a graphical representation of a patient's torso and external electrode apparatus configured to measure global and local electrical activity.

Exemplary external electrode apparatus 110 that may be used to monitor global and local, or regional, electrical activity for the generation of global and local electrical heterogeneity information is depicted in FIG. 5. As shown, the external electrode apparatus 110 includes a strap 115 about the torso 300 of a patient. A plurality of electrodes are located and distributed about the strap 115 around the torso 300 of the patient. All of the electrodes of the external electrode apparatus 115 may be used to monitor global electrical activity of the patient for generation of global electrical heterogeneity information. Left electrodes, which are indicated as being proximate the patient's left side within dotted outline 302, may be used to compute local, or regional, left electrical heterogeneity information. It is to be understood that the left region denoted by the dotted outline 302 is merely one example of the "left" electrodes, and the left region may be smaller or larger and/or located in a different location than shown.

The left electrodes may be defined as any surface electrodes located proximate the patient's left ventricle, which includes one or more regions to left of the patient's sternum and spine. In one embodiment, the left electrodes may include all anterior electrodes on the left of the sternum and all posterior electrodes to the left of the spine. In another embodiment, the left electrodes may include all anterior electrodes on the left of the sternum and all posterior electrodes. In yet another embodiment, the left electrodes may be designated based on the contour of the left and right sides of the heart as determined using imaging apparatus (e.g., x-ray, fluoroscopy, etc.).

Another metric, or index, of electrical heterogeneity may be a left standard deviation of surrogate electrical activation times (LVED) monitored by external electrodes located proximate the left side of patient. Further, another metric, or index, of electrical heterogeneity may include an average of surrogate electrical activation times (LVAT) monitored by external electrodes located proximate the left side of patient. The LVED and LVAT may be determined (e.g., calculated, computed, etc.) from electrical activity measured only by the left electrodes (e.g., the electrodes proximate the left side of the patient).

Another exemplary metric, or index, of dyssynchrony may be a range of activation times (RAT) that may be computed as the difference between the maximum and the minimum torso-surface or cardiac activation times, e.g., overall, or for a region. The RAT reflects the span of activation times while the SDAT gives an estimate of the dispersion of the activation times from a mean. The SDAT also provides an estimate of the heterogeneity of the activation times, because if activation times are spatially heterogeneous, the individual activation times will be further away from the mean activation time, indicating that one or more regions of heart have been delayed in activation. In some examples, the RAT may be calculated using the estimated cardiac activation times over the surface of a model heart.

Another exemplary metric, or index, of electrical heterogeneity information may include estimates of a percentage of surface electrodes located within a particular region of interest for the torso or heart whose associated activation times are greater than a certain percentile, such as, for example the 70th percentile, of measured QRS complex duration or the determined activation times for surface electrodes. The region of interest may, e.g., be a posterior, left anterior, and/or left-ventricular region. The exemplary metric, or index, may be referred to as a percentage of late activation (PLAT). The PLAT may be described as providing an estimate of percentage of the region of interest, e.g., posterior and left-anterior area associated with the left ventricular area of heart, which activates late. A large value for PLAT may imply delayed activation of a substantial portion of the region, e.g., the left ventricle, and the potential benefit of electrical resynchronization through CRT by pre-exciting the late region, e.g., of left ventricle. In other examples, the PLAT may be determined for other subsets of electrodes in other regions, such as a right anterior region to evaluate delayed activation in the right ventricle. Furthermore, in some examples, the PLAT may be calculated using the estimated cardiac activation times over the surface of a model heart for either the whole heart or for a particular region, e.g., left or right ventricle, of the heart.

In one or more embodiments, the cardiac information may include indicators of favorable changes in global cardiac electrical activation such as, e.g., described in Sweeney et al., "Analysis of Ventricular Activation Using Surface Electrocardiography to Predict Left Ventricular Reverse Volumetric Remodeling During Cardiac Resynchronization Therapy," Circulation, 2010 Feb. 9, 121(5): 626-34 and/or Van Deursen, et al., "Vectorcardiography as a Tool for Easy Optimization of Cardiac Resynchronization Therapy in Canine LBBB Hearts," Circulation Arrhythmia and Electrophysiology, 2012 Jun. 1, 5(3): 544-52, each of which is incorporated herein by reference in its entirety. Cardiac information may also include measurements of improved cardiac mechanical function measured by imaging or other systems to track motion of implanted leads within the heart as, e.g., described in Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, 2010 February, 21(2): 219-22, Sperzel et al., "Intraoperative Characterization of Interventricular Mechanical Dyssynchrony Using Electroanatomic Mapping System—A Feasibility Study," Journal of Interventional Cardiac Electrophysiology, 2012 November, 35(2): 189-96, and/or U.S. Pat. App. Pub. No. 2009/0099619 A1 entitled "METHOD FOR OPTIMIZAING CRT THERAPY" and published on Apr. 16, 2009, each of which is incorporated herein by reference in its entirety.

The exemplary method 200 may then generate surrogate hemodynamic response information 210 based on the baseline electrical heterogeneity information and therapy electrical heterogeneity information. The surrogate hemodynamic response information may be representative of the hemodynamic response to the pacing therapy delivered using the selected pacing configuration. For example, the surrogate hemodynamic response information may correlate to a change in left ventricular contractility as compared to a baseline (e.g., where contractility is measured as the maximum rate of left ventricular pressure rise). Left ventricular contractility and/or pressure may be typically monitored invasively with a pressure sensor located in the left ventricle of a patient's heart. As such, the use of electrical heterogeneity information to generate, or determine, a surrogate value representative of the left ventricular contractility may avoid invasive monitoring using a left ventricular pressure sensor.

The surrogate hemodynamic response information may be generated 210 using both of the baseline electrical heterogeneity information and therapy electrical heterogeneity information. In one or more embodiments, the baseline electrical heterogeneity information and therapy electrical heterogeneity information may be compared to each other to provide a change, or delta, value. For example, the therapy SDAT may be subtracted from the baseline SDAT to generate a change in SDAT. Likewise, for example, the therapy LVED and LVAT may be subtracted from the baseline LVED and LVAT generate a change in LVED and LVAT, respectively. These changes in SDAT, LVED, and LVAT may be used by the transfer function to generate the surrogate hemodynamic response information.

The generation of surrogate hemodynamic response information 210 may utilize a transfer function. Generally, the transfer function may receive the electrical heterogeneity information and may output the surrogate hemodynamic response information based on the received electrical heterogeneity information. The transfer function may be calculated, or generated, based on data gathered from patients undergoing cardiac therapy that is adjusted to provide effective therapy. The data may include external electrical activity of the patient and electrical heterogeneity information that is generated from the external electrical activity.

Further, the data used to calculate the transfer function may include a plurality of parameters different from the external electrical activity and electrical heterogeneity information that are indicative of hemodynamic response of the patient. For example, a pressure sensor may be located in one or more chambers (e.g., left ventricle) of the patient's heart to monitor hemodynamics of the patient's heart before and/or during therapy. The plurality of parameters may include left ventricular contractility, ejection fraction, end-systolic volume, cardiac output, left atrial pressure, arterial pressure, arterial oxygen saturation, aortic volumes, and other related metrics indicative of cardiac function and hemodynamics.

The transfer function may be described as a multivariable prediction model created using a change in SDAT (delSDAT), a change in LVED (delved), and a change in LVAT (delLVAT) as the inputs, and a change in left ventricular contractility (e.g., dp/dt, change in maximum left ventricular pressure rate, etc.) as the output. In at least one embodiment, a Gradient tree boosting algorithm may be used to develop the model. Gradient boosting may be described as a machine learning technique for regression problems, which, may produce a prediction model in the form of an ensemble of weak prediction models (e.g., decision trees). Further, gradient boosting may build a model in a stage-wise fashion (e.g., similar to other boosting methods) and may generalize the predication models by allowing optimization of an arbitrary differentiable loss function. In addition, cross validation may be used to protect against "over fitting" the model as well as optimizing hyper parameters. The implementation of gradient boosting algorithm for doing predictions may be a grid search. To develop the grid, the predictive model may be implemented as described herein for an exhaustive set of combinations of the inputs and to determine the outputs to each one of those combinations with the results saved in a grid format, which may be referenced.

Other exemplary transfer functions may be generated using exemplary data mining methods such as, e.g., Gaussian processes, support vector machines, random forests, Bayesian networks, neural networks, etc. Additional exemplary methods may be described in Y. Freund and R. E. Schapire, (1997), "A decision-theoretic generalization of online learning and an application to boosting," Journal of Computer and System Sciences, 55(1):119-139, J. H. Friedman (2001), "Greedy Function Approximation: A Gradient Boosting Machine," Annals of Statistics 29(5):1189-1232, J. H. Friedman (2002), "Stochastic Gradient Boosting," Computational Statistics and Data Analysis 38(4):367-378, J. H. Friedman, T. Hastie, R. Tibshirani (2000), "Additive Logistic Regression: a Statistical View of Boosting, Annals of Statistics 28(2):337-374, G. Ridgeway (1999), The state of boosting," Computing Science and Statistics 31:172-181, each of which is incorporated herein by reference in its entirety.

The transfer function may be described as a function of the generated electrical information configured to compute, or generate, output that includes one or more of the plurality of parameters (e.g., the plurality of parameters monitored to create the function). More specifically, one or more metrics, or indices, of electrical heterogeneity information may be input into an exemplary transfer function and one or more metrics, or indices, representative of hemodynamic response may be output by the exemplary transfer function. For example, one or more metrics, or indices, of electrical heterogeneity information may be input into an exemplary transfer function and an acute response such as, e.g., left ventricular contractility (e.g., maximum left ventricular pressure rate), may be output by the transfer function. Or, for example, one or more metrics, or indices, of electrical heterogeneity information may be input into an exemplary transfer function and a chronic response such as, e.g., ejection fraction, may be output by the transfer function.

A more detailed portion of the exemplary method 200 is depicted in FIG. 6. As shown, generating electrical heterogeneity information may include generating one or more global metrics, or indices, of electrical heterogeneity information 212 and one or more local metrics, or indices, of electrical heterogeneity information 214. In at least one embodiment, the one or more global metrics 212 include SDAT and the one or more local metrics 214 include LVED and LVAT.

In one or more embodiments, the baseline and therapy global metrics 212 and local metrics 214 of electrical heterogeneity information may be input into the transfer function 216 to generate the surrogate hemodynamic response information. In one or more other embodiments, the change between, or delta of, the baseline and therapy global metrics 212 and local metrics 214 of electrical heterogeneity information may be input into the transfer function 216 to generate the surrogate hemodynamic response information.

Further, the transfer function may give different significance, or influence, to each of the input values. An input having more significance or influence may affect the output greater than an input having less significance or influence.

Likewise, an input having less significance or influence may affect the output less than an input having greater significance or influence. For example, change in LVED may be given a greater significance (e.g., about 50%) than change in LVAT (e.g., about 30%), and change in LVAT (e.g., about 30%) may be given a greater significance than change in SDAT (e.g., about 20%). In other words, each of the electrical heterogeneity metrics, or indices, used by the transfer function to generate the surrogate hemodynamic response information may be given different weight. The weight, or significance, of each of the electrical heterogeneity metrics, or indices, may be determined during, or with, the generation of the transfer function.

The surrogate hemodynamic response information may include one more difference pieces of information such as, e.g., values, graphical representations, graphs, bar charts, color codes, color-coded maps, representations of directional and/or magnitude of differences between current and prior measurements, etc. In this example, the surrogate hemodynamic response information includes at least a hemodynamic response value 218 (e.g., a stochastic estimate with a high level of confidence). The hemodynamic response value 218 may be a value representative of the hemodynamic improvement due to the pacing therapy delivered using the selected pacing configuration.

In at least one embodiment, the hemodynamic response value 218 may correlate to left ventricular contractility (e.g., left ventricular pressure rate). The correlation between the hemodynamic response value 218 and left ventricular contractility (e.g., maximum left ventricular pressure rate) may be greater than or equal to about 70%. For example, the transfer function may have a coefficient of determination ($R^2$) between the hemodynamic response value 218 and the left ventricular contractility (e.g., maximum left ventricular pressure rate) that is greater than or equal to 60%. The hemodynamic response value 218 may conveyed to a user (e.g., a physician), e.g., using a graphical user interface displayed by a display apparatus, etc. Further, multiple hemodynamic response values 218 for multiple different pacing configurations may be conveyed to a user simultaneously such that, e.g., a user may determine whether the hemodynamic response is improving.

As further shown in FIG. 6, the hemodynamic response value 218 and/or other surrogate hemodynamic response information may be evaluated to determine whether the pacing therapy using the pacing configuration is acceptable 220. For example, if the hemodynamic response value is greater than or equal to a threshold value, then the pacing configuration may be determined to be acceptable. The threshold value may vary considerably depending on the transfer function. In one or more embodiments, the threshold value may be a percentage, or ratio, of the improvement of the hemodynamic response from baseline. For example, a hemodynamic response value 218 may be generated for each of the baseline heterogeneity information and the therapy baseline heterogeneity information and the therapy heterogeneity information may be divided by the baseline heterogeneity information to generate the percentage, or ratio, of the improvement of the hemodynamic response from baseline.

The threshold value may be greater than or equal to about 5%, greater than or equal to about 10%, greater than or equal to about 15%, greater than or equal to about 20%, greater than or equal to about 25%, greater than or equal to about 35%, greater than or equal to about 45%, etc. Further, the threshold value may be less than or equal to about 60%, less than or equal to about 50%, less than or equal to about 40%, less than or equal to about 30%, less than or equal to about 20%, less than or equal to about 17%, etc.

If the hemodynamic response value is acceptable (e.g., indicative of effective cardiac therapy, indicative of an improvement in hemodynamic response, etc.), a user may stop configuring the cardiac therapy and may program the cardiac therapy apparatus with the parameters as configured or adjusted. If the hemodynamic response value is not acceptable (e.g., indicative ineffective cardiac therapy, not indicative of an improvement in hemodynamic response, etc.), a user may continue adjusting or configuring the cardiac therapy once (e.g., change the pacing configuration), and the exemplary systems and methods described herein may evaluate the newly-adjusted, or configured, therapy. More specifically, a user may adjust one or more parameters of the pacing configuration such that the pacing configuration is different than the previous pacing configuration. For example, a user may select a different pacing vector, or may move the pacing electrode. Further, for example, a user may change the pacing power output. Then, the new pacing configurations may be evaluated by the method 200. A user may continue configuring the pacing therapy and evaluating the pacing therapy using method 200 until, e.g., the user determines that the pacing therapy has been optimally or acceptably configured.

As described herein with reference to FIG. 1, the exemplary systems and methods described herein may use display apparatus 130 including a graphical user interface 132. The graphical user interface 132 may be configured to, among other things, present information for use in assisting a user in evaluating cardiac pacing, in configuring the cardiac therapy, in assisting a user in navigating at least one implantable electrode to a region of the patient's heart, etc. For example, the graphical user interface 132 may be configured to display a graphical representation of electrical heterogeneity information and surrogate hemodynamic response information determined by method 200.

Figure 7:
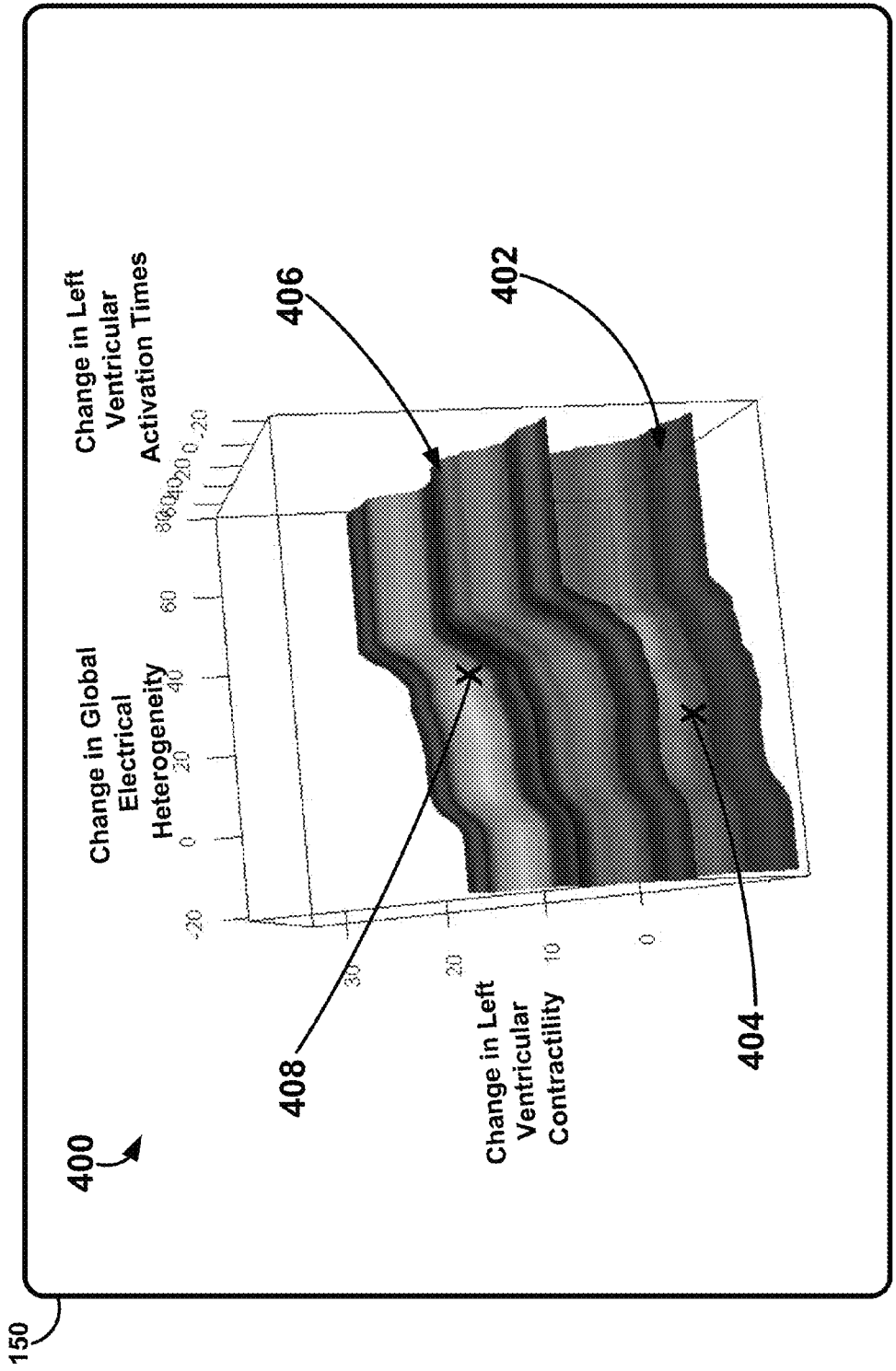
FIG. 7 is an exemplary graphical user interface depicting a graphical representation of surrogate hemodynamic response information.

An exemplary graphical user interface (GUI) 150 for use in evaluating and/or configuring cardiac therapy is depicted in FIG. 7. As shown, the graphical representation is a 3-axis graph 400 with the electrical heterogeneity information along the X and Z axes and the surrogate hemodynamic response information along the Y axis. More specifically, change in global electrical heterogeneity (SDAT) is shown along the X axis, change in left ventricular activation times (LVAT) is shown along the Z axis, and change in left ventricular contractility (e.g., maximum left ventricular pressure rate) is shown along the Y axis.

Two different pacing configurations are depicted in the graph 400. The first pacing configuration is represented by the marker ("X") 404 shown with the transfer function representation 402. The transfer function representation 402 may be depicted such that a user may see on the graph 400 that the transfer function indicates, or predicts, that hemodynamic improvement may be achieved if the marker is located in a "low" spot (e.g., low on the Y axis, which is change in maximum left ventricular pressure) on the transfer function representation 402. For instance, the transfer function representation may include portions that are located "higher" on the Y axis, which indicates that the transfer function predicts that cardiac therapy may be further configured to provide greater output (e.g., greater change in maximum left ventricular pressure).

The second pacing configuration is represented by the marker ("X") 408 shown with the transfer function representation 406. As shown, the second pacing configuration appears to have significantly improved in all three depicted metrics. It is to be understood that the graphical representation shown in FIG. 7 is merely one example, and that the electrical heterogeneity information, surrogate hemodynamic response information, and the transfer function may be depicted many different ways. For example, the electrical heterogeneity information, surrogate hemodynamic response information, and the transfer function may be depicted using alphanumeric values, graphical representations, graphs, bar charts, color codes, color-coded maps, representations of directional and/or magnitude of differences between current and prior measurements, etc.

The exemplary systems, methods, and graphical user interfaces described herein may be used with respect to the implantation and configuration of an implantable medical device (IMD) and/or one or more leads configured to be located proximate one or more portions of a patient's heart. For example, the exemplary systems, methods, and interfaces may be used in conjunction with an exemplary therapy system 10 described herein with reference to FIGS. 8-10.

Figure 8:
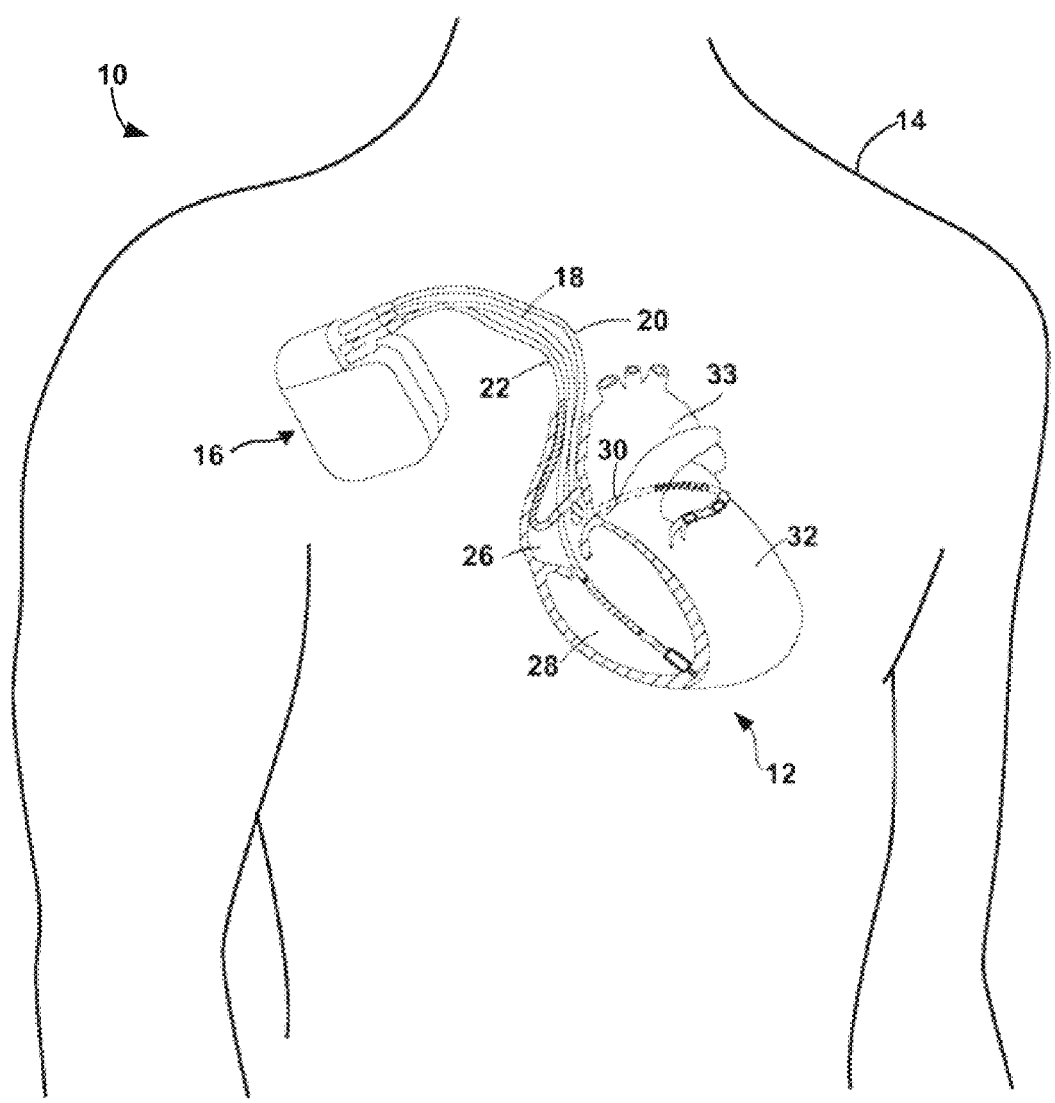
FIG. 8 is a diagram of an exemplary system including an exemplary implantable medical device (IMD).

FIG. 8 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 8, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse wide, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 9A:
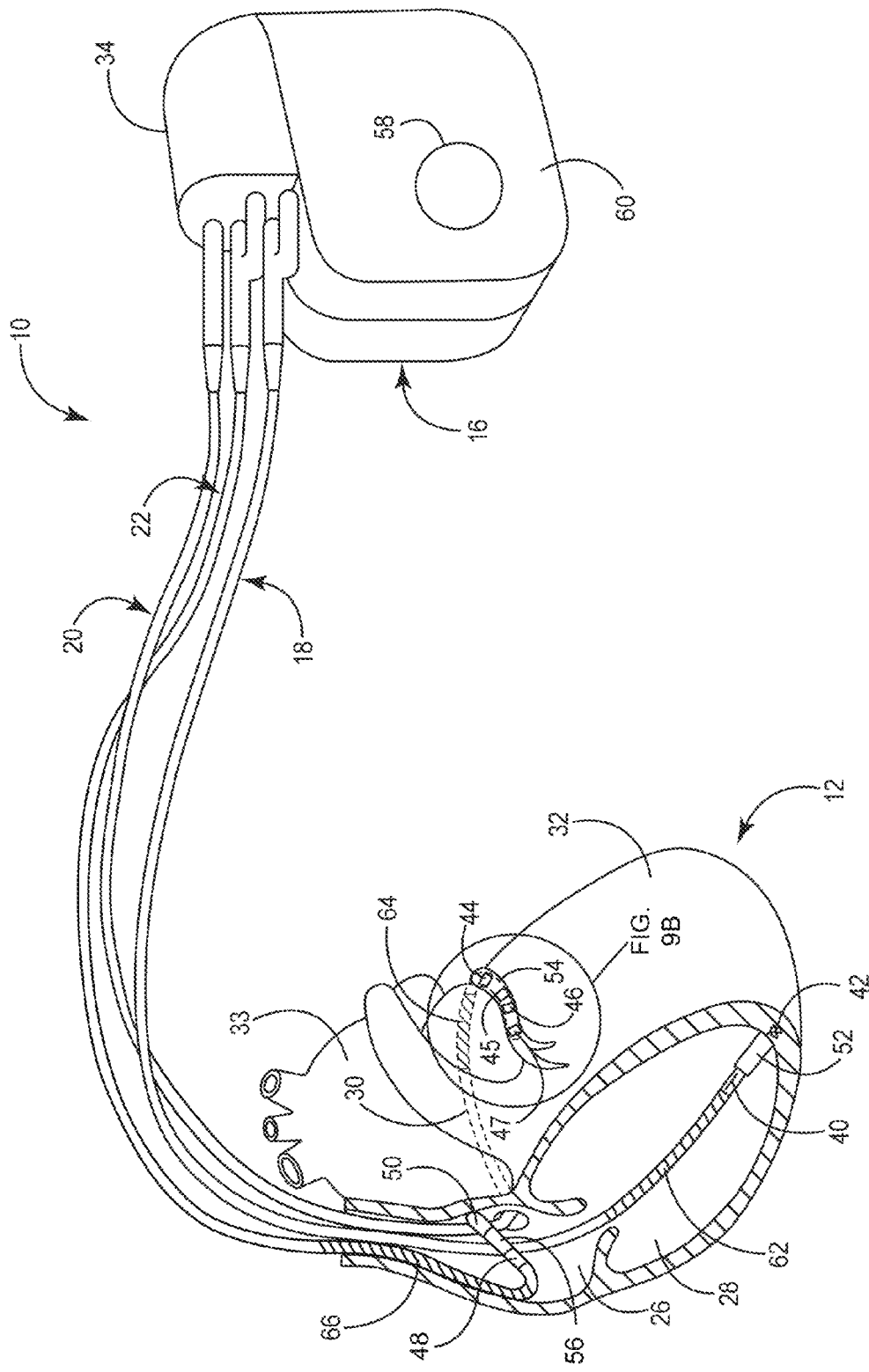
FIG. 9A is a diagram of the exemplary IMD of FIG. 8.
Figure 9B:
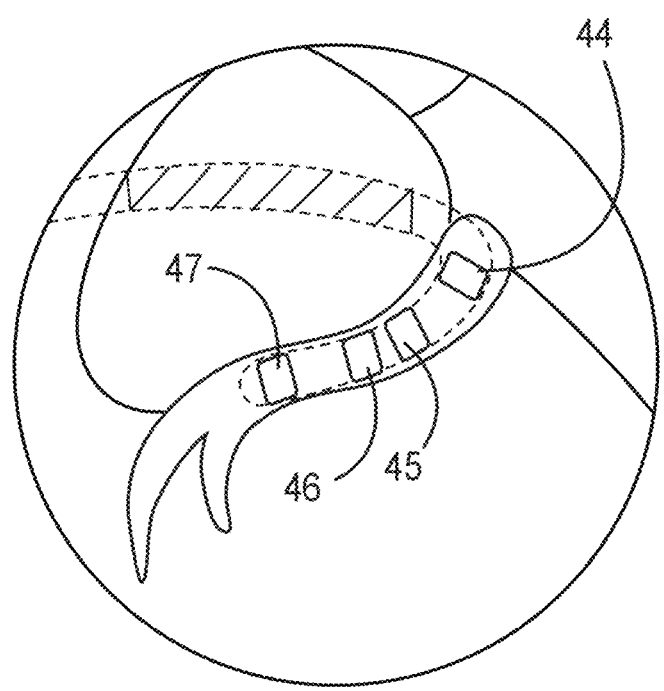
FIG. 9B is a diagram of an enlarged view of a distal end of the electrical lead disposed in the left ventricle of FIG. 9A.

FIGS. 9A-9B are conceptual diagrams illustrating the IMD 16 and the leads 18, 20, 22 of therapy system 10 of FIG. 8 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 9A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 9A, the housing 60 may enclose a therapy delivery module that may include a stimulation generator for generating cardiac pacing pulses and defibrillation or cardioversion shocks, as well as a sensing module for monitoring the electrical signals of the patients heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the exemplary therapy systems 10 illustrated in FIGS. 8-10 is merely one example. In other examples, the therapy system may include epicardial leads and/or patch electrodes instead of or in addition to the transvenous leads 18, 20, 22 illustrated in FIG. 8. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 8). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 9-11. Still further, other therapy systems may include a single lead that extends from the IMD 16 into the right atrium 26 or the right ventricle 28, or two leads that extend into a respective one of the right atrium 26 and the right ventricle 28.

Figure 10A:
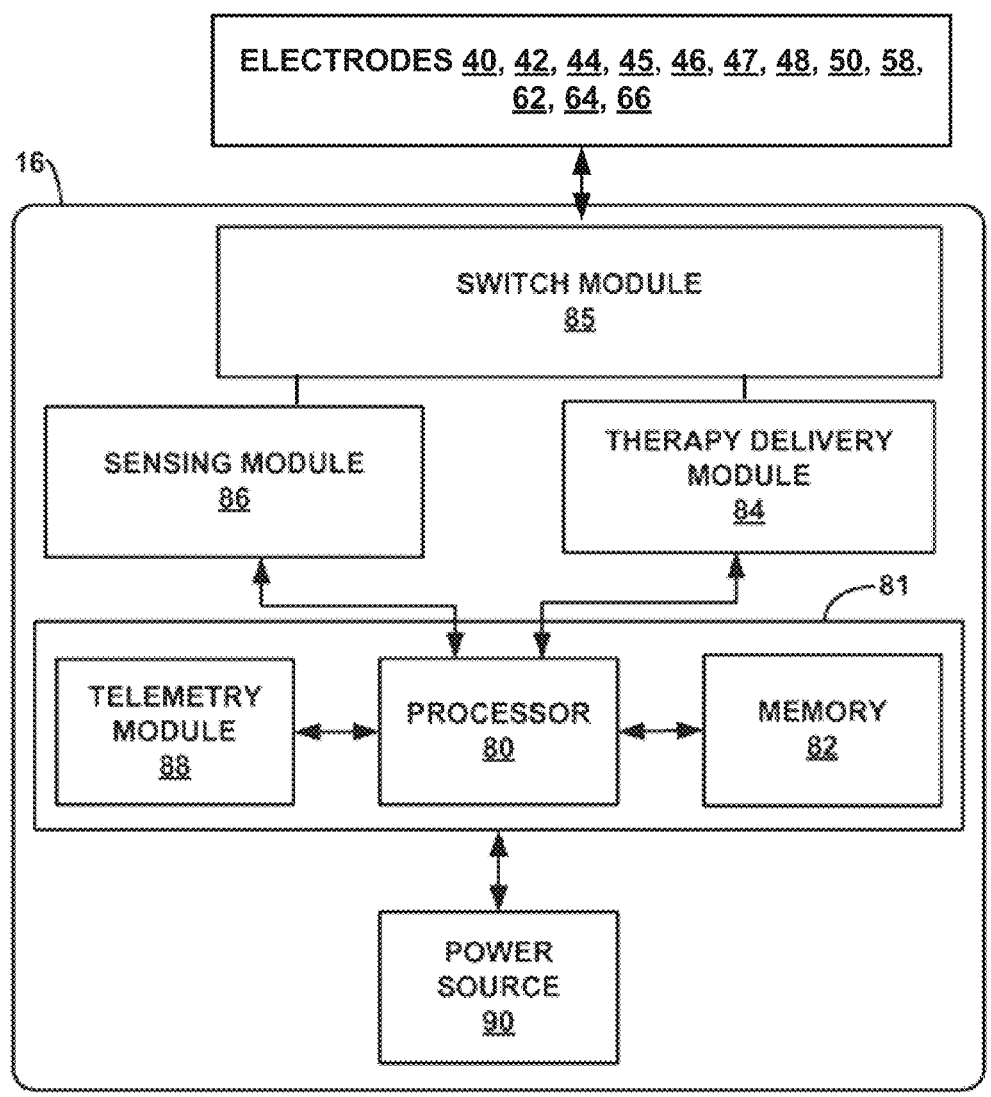
FIG. 10A is a block diagram of an exemplary IMD, e.g., of the systems of FIGS. 8-9.

FIG. 10A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, VV delays, pacing pulses with the amplitudes, pulse widths, frequency, or electrode polarities, etc., which may be specified by one or more selected therapy programs (e.g., AV and/or VV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 10B:
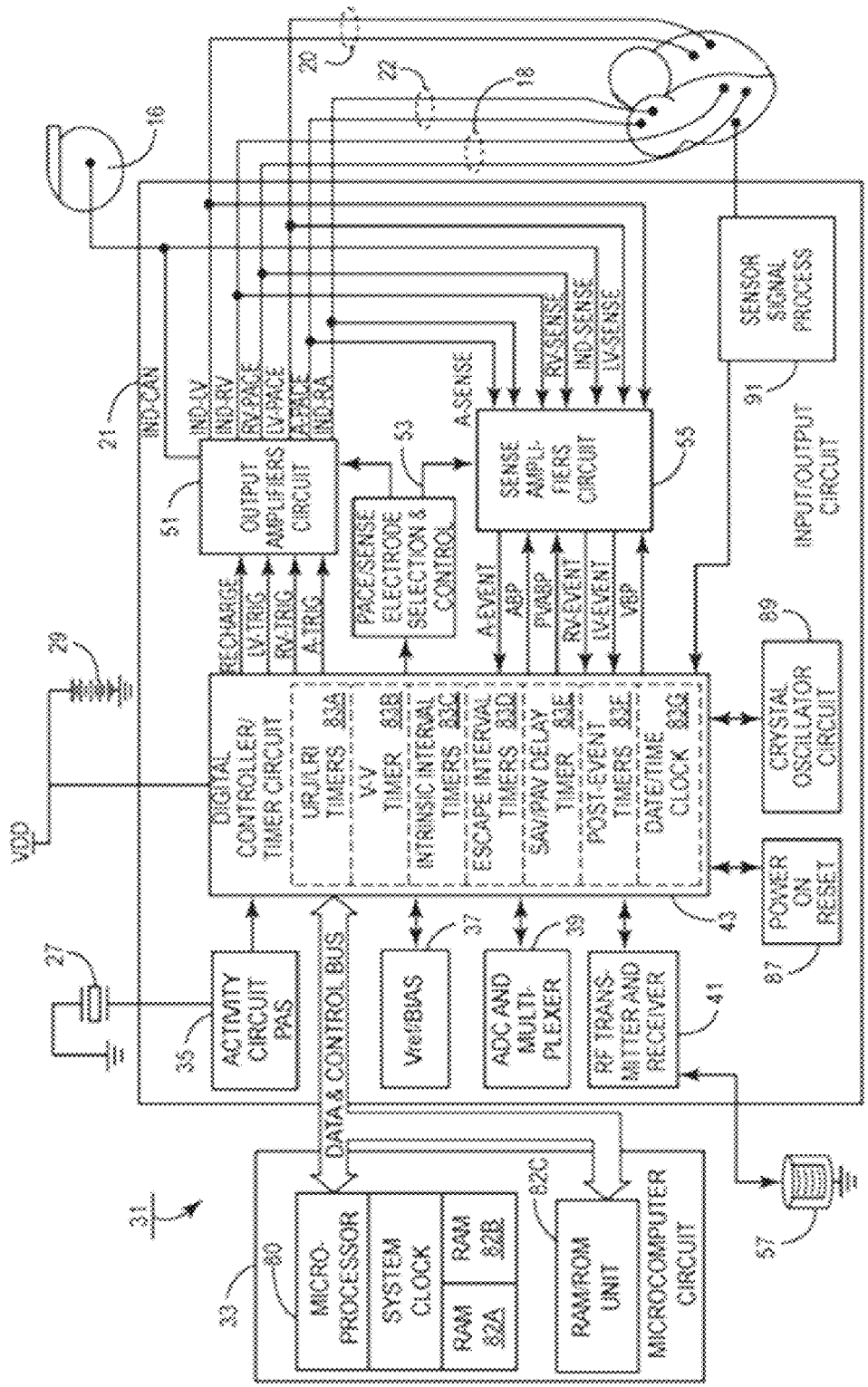
FIG. 10B is another block diagram of an exemplary IMD (e.g., an implantable pulse generator) circuitry and associated leads employed in the systems of FIGS. 8-9.

FIG. 10B is another embodiment of a functional block diagram for IMD 16. FIG. 10B depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in exemplary implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer. The output signal of the patient activity sensor 27 may be processed and used as a RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in its entirety. Similarly, the exemplary systems, apparatus, and methods described herein may be practiced in conjunction with alternate types of sensors such as oxygenation sensors, pressure sensors, pH sensors, and respiration sensors, for use in providing rate responsive pacing capabilities. Alternately, QT time may be used as a rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals, V-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, VV delays, post-ventricular time periods, and post-atrial time periods that vary with the sensor based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system for use in evaluation of cardiac therapy comprising:
    electrode apparatus comprising a plurality of external electrodes configured to be located proximate tissue of a patient, wherein the plurality of electrodes comprises two or more left external electrodes configured to be located proximate the left side of the patient; and
    computing apparatus coupled to the electrode apparatus and configured to:
       monitor baseline electrical activity using the plurality of external electrodes,
       monitor therapy electrical activity using the plurality of external electrodes during delivery of pacing therapy using a selected pacing configuration, generate electrical heterogeneity information representative of at least one of mechanical cardiac functionality and electrical cardiac functionality for each of the baseline electrical activity and the therapy electrical activity, wherein the electrical heterogeneity information comprises:
 a global metric based on the electrical activity monitored by the plurality of external electrodes, and
 at least one local metric based on the electrical activity monitored by the two or more left external electrodes, and
generate surrogate hemodynamic response information representative of the hemodynamic response to the pacing therapy delivered using the selected pacing configuration based on the electrical heterogeneity information for each of the baseline electrical activity and the therapy electrical activity.

2. The system of claim 1, wherein generating surrogate hemodynamic response information representative of the hemodynamic response to the pacing therapy delivered using the selected pacing configuration based on the electrical heterogeneity information for each of the baseline electrical activity and the therapy electrical activity comprises:
providing a transfer function configured to receive the global metric and the at least one local metric to generate surrogate hemodynamic response information correlating to left ventricular contractility, wherein the transfer function provides a coefficient of determination ($R^2$) between the surrogate hemodynamic response information and the left ventricular contractility that is greater than or equal to 60%;
inputting the global metric and the at least one local metric into the transfer function; and
generating the hemodynamic response information correlating to left ventricular contractility using the transfer function based on the global metric and the at least one local metric.

3. The system of claim 1, wherein the pacing therapy is delivered by at least one implantable electrode coupled to at least one lead, wherein the hemodynamic response information is configured to assist a user in non-invasively selecting an implant location for the at least one implantable electrode coupled to the at least one lead.

4. The system of claim 1, wherein the at least one local metric comprises at least one of a left standard deviation of surrogate electrical activation times monitored by the two or more left external electrodes and a left average of surrogate electrical activation times monitored by the two or more left external electrodes.

5. The system of claim 1, wherein the global metric comprises a global standard deviation of surrogate electrical activation times monitored by the plurality of external electrodes.

6. The system of claim 1, wherein the selected pacing configuration comprises one or more pacing settings, wherein the one or more pacing settings comprise one or more of A-V intervals, V-V intervals, pacing vectors, pacing energy outputs, pacing locations, and multipoint pacing timings.

7. The system of claim 6, wherein the pacing vector comprises a multipoint pacing vector.

8. The system of claim 1, wherein the selected pacing configuration comprises cathode location.

9. The system of claim 1, wherein the hemodynamic response information comprises a hemodynamic response value representative of the hemodynamic improvement due to the pacing therapy delivered using the selected pacing configuration.

10. The system of claim 9, wherein the computing apparatus is further configured to determine whether the pacing therapy using the pacing configuration is acceptable if the hemodynamic response value is greater than or equal to a threshold value.

11. The system of claim 1, wherein the plurality of external electrodes comprises surface electrodes positioned in an array configured to be located proximate the skin of the torso of the patient.

12. The system of claim 1, wherein the system further comprises display apparatus, wherein the display apparatus comprises a graphical user interface configured to present information for use in assisting a user in evaluating cardiac pacing location,
wherein the computing apparatus is further configured to display the hemodynamic response information on the graphical user interface.

13. The system of claim 12, wherein the computing apparatus is further configured to display a graphical representation of the hemodynamic response information.

14. A method for use in evaluation of cardiac therapy comprising:
providing electrode apparatus comprising a plurality of external electrodes configured to be located proximate tissue of a patient, wherein the plurality of electrodes comprises two or more left external electrodes configured to be located proximate the left side of the patient;
monitoring baseline electrical activity using the plurality of external electrodes;
monitoring therapy electrical activity using the plurality of external electrodes during delivery of pacing therapy using a selected pacing configuration;
generating electrical heterogeneity information representative of at least one of mechanical cardiac functionality and electrical cardiac functionality for each of the baseline electrical activity and the therapy electrical activity, wherein the electrical heterogeneity information comprises:
 a global metric based on the electrical activity monitored by the plurality of external electrodes, and
 at least one local metric based on the electrical activity monitored by the two or more left external electrodes; and
generating surrogate hemodynamic response information representative of the hemodynamic response to the pacing therapy delivered using the selected pacing configuration based on the electrical heterogeneity information for each of the baseline electrical activity and the therapy electrical activity.

15. The method of claim 14, wherein generating surrogate hemodynamic response information representative of the hemodynamic response to the pacing therapy delivered using the selected pacing configuration based on the electrical heterogeneity information for each of the baseline electrical activity and the therapy electrical activity comprises:
providing a transfer function configured to receive the global metric and the at least one local metric to generate surrogate hemodynamic response information correlating to left ventricular contractility, wherein the transfer function provides a coefficient of determination ($R^2$) between the surrogate hemodynamic response information and the left ventricular contractility that is greater than or equal to 60%;

inputting the global metric and the at least one local metric into the transfer function; and generating the hemodynamic response information correlating to left ventricular contractility using the transfer function based on the global metric and the at least one local metric.

16. The method of claim 14, wherein the pacing therapy is delivered by at least one implantable electrode coupled to at least one lead, wherein the hemodynamic response information is configured to assist a user in non-invasively selecting an implant location for the at least one implantable electrode coupled to the at least one lead.

17. The method of claim 14, wherein the at least one local metric comprises at least one of a left standard deviation of surrogate electrical activation times monitored by the two or more left external electrodes and a left average of surrogate electrical activation times monitored by the two or more left external electrodes.

18. The method of claim 14, wherein the global metric comprises a global standard deviation of surrogate electrical activation times monitored by the plurality of external electrodes.

19. The method of claim 14, wherein the selected pacing configuration comprises one or more pacing settings, wherein the one or more pacing settings comprise one or more of A-V intervals, V-V intervals, pacing vectors, pacing energy outputs, pacing locations, and multipoint pacing timings.

20. The system of claim 19, wherein the pacing vector comprises a multipoint pacing vector.

21. The method of claim 14, wherein the selected pacing configuration comprises cathode location.

22. The method of claim 14, wherein the hemodynamic response information comprises a hemodynamic response value representative of the hemodynamic improvement due to the pacing therapy delivered using the selected pacing configuration.

23. The system of claim 22, wherein the method further comprises determining whether the pacing therapy using the pacing configuration is acceptable if the hemodynamic response value is greater than or equal to a threshold value.

24. The method of claim 14, wherein the plurality of external electrodes comprises surface electrodes positioned in an array configured to be located proximate the skin of the torso of the patient.

25. The method of claim 14, wherein the method further comprises displaying the hemodynamic response information on a graphical user interface configured to present information for use in assisting a user in evaluating cardiac pacing location.

26. The method of claim 25, wherein the method further comprises displaying a graphical representation of the hemodynamic response information.

* * * * *